US00RE36434E

United States Patent [19]

Hamlin et al.

[11] E Patent Number: Re. 36,434

[45] **Reissued Date of Patent: *Dec. 7, 1999**

[54] ENDOSCOPIC DEVICE

[76] Inventors: David Hamlin, 109 Rugby Dr., Langhorne, Pa. 19047; Arthur C. McKinley, 11 Academy Ave., Bradford, Mass. 01835; William Habermann, 22 Slabtown Creek Rd., Blairstown, N.J. 07825

[ * ] Notice: This patent is subject to a terminal disclaimer.

[21] Appl. No.: 09/198,099

[22] Filed: Nov. 23, 1998

Related U.S. Patent Documents

Reissue of:

[64] Patent No.: 5,690,605
Issued: Nov. 25, 1997
Appl. No.: 08/426,608
Filed: Apr. 19, 1995

U.S. Applications:

[63] Continuation-in-part of application No. 08/148,097, Nov. 5, 1993, Pat. No. 5,408,992.

[51] Int. Cl.[6] ..... A61B 1/04

[52] U.S. Cl. ..... 600/109; 600/121; 600/125; 600/160; 600/170

[58] Field of Search ..... 600/109, 121, 600/125, 112, 111, 160, 166, 170, 171, 172, 173; 433/29; 359/654, 643, 368, 385, 716, 708, 784

[56] References Cited

U.S. PATENT DOCUMENTS 4,850,342 7/1989 Hashiguchi .
4,862,873 9/1989 Yajima et al. .
4,878,485 11/1989 Adair .
5,408,992 4/1995 Hamlin et al. .

*Primary Examiner*—John P. Leubecker
*Attorney, Agent, or Firm*—Donald S. Cohen

[57] ABSTRACT

An endoscopic device includes an endoscopic tube for insertion into a cavity to be viewed; an optical system including a video camera and illuminating means for viewing the cavity, the image on the screen being a noninverted image; and a removable, rigid, sterilizable or discardable sheath completely enclosing the endoscopic tube and the illuminating means to prevent their exposure to the cavity environment.

14 Claims, 4 Drawing Sheets

ENDOSCOPIC DEVICE

Matter enclosed in heavy brackets [ ] appears in the original patent but forms no part of this reissue specification; matter printed in italics indicates the additions made by reissue.

RELATED APPLICATIONS

This application is a continuation-in-part of Ser. No. 08/148,097, filed Nov. 5, 1993 now U.S. Pat. No. 5,408,992.

FIELD OF THE INVENTION

This invention relates to a device having an nonreversing imaging system and particularly to a device having an autoclavable endoscopic or bore-scope for viewing internal structures on a video screen, wherein the image is not reversed with respect to the user. More particularly, the preferred embodiment provides an autoclavable sheath and a non-reversed imaging system which may further include a handpiece adapter for use in such a system.

BACKGROUND OF THE INVENTION

Bore-scopes, endoscopes and similar devices for viewing internal body structures and cavities on a video screen utilizing an imaging device and a video camera are well known. Such devices have been used widely in the medical field for viewing internal human tissue and in industry for inspecting the hidden surfaces of various structures.

A typical endoscopic system comprises an endoscopic lens device, a video camera and a video display and/or storage media. The endoscopic device comprises a supporting member, having a forward end to which there is attached an endoscopic tube which enters the internal cavity to be viewed. The endoscopic tube in some cases, but not all (some systems rely on ambient lighting), contains a light guide connected to a light source. e.g. a fiber optic bundle for illuminating the surfaces within the cavity and a lens system for conveying light reflected from these surfaces back to the video camera. The video camera is generally mounted on the supporting member opposite the endoscopic tube. Low level electrical signals developed by the camera (e.g. a CCD Chip) are conveyed through appropriate wires to a signal processing device for creating a video display and/or recording a video image. In some smaller endoscopic systems (e.g. intraoral devices), the endoscopic tube is directly coupled to an SCR camera without an intervening support member.

For infection control, one recent requirement for such devices is that any portion of the device which enters a body cavity must be either discarded or sterilized before reuse. Generally, in previous apparatus, e.g. the intraoral camera system marketed by AcuCam of Canoga Park, Calif., the entire forward end of the endoscopic device, including the light guide and lens system, is detached from the camera for sterilization. Since sterilization, e.g. by autoclaving, is generally time consuming, the dentist would require several expensive lens-fiber optic system members to be on hand for use with subsequent patients. Further, repeated sterilization can degrade or damage the optics and light guides. Hence, a need exists for a device which would allow immediate reuse of a lens-fiber optic system member without delay, damage, or inventory expense associated with the necessity of sterilization.

Another shortcoming of the aforementioned intraoral system is that the same member which is inserted into the oral cavity is held by the user. While the user (dentist) generally wears protective gloves and the portion held is generally a short distance from the inserted portion of the device, it would still be safer for both the user and the patient, that the user should not have to hold that portion of the device at all while in use. Any surface not being exposed directly, either external or internal to the patient's body cavity is considered an environmental surface and is/can be treated by appropriate high level disinfection rather than by sterilization.

A further disadvantage of prior art devices is that the image displayed on the screen is the mirror image of the actual field being observed. In such a system, movement by the manipulator of the device in one direction, e.g. the left, appears as movement in the opposite direction, e.g. the right, on the screen. This often leads to a difficulty of interpretation of orientation and manipulation of the device. It is therefore deskable to employ an imaging system wherein the image viewed on the screen is not reversed with respect to the actual movement of the device by its user.

Still another disadvantage occurring with respect to the prior art intraoral system is that the bulkiness or size of the inserted portion tends to block the vision of the user with respect to the oral cavity and the patient may tend to gag.

Yet another disadvantage of some intraoral systems is that the optical system is not sealed from the oral (or other) cavity thereby requiring sterilization of that member containing that system after each use. Such shortcomings are difficult or impossible to address without potential fatal damage to precision electronics and optics.

The novel device may substantially eliminate the above problems.

SUMMARY OF THE INVENTION

An endoscopic device for viewing, on a screen, a field within a cavity comprising illuminating means for illuminating the field to be viewed; optical means for transmitting and focussing light reflected from the illuminated field onto the plane of a video camera or other image detector in a manner wherein the image potrayed on the screen is not reversed with respect to the actual field being viewed. The preferred embodiment further comprising a handle; means associated with said handle for mounting an image detector e.g. a video camera; a rigid optics tube mounted to said handle, said optics tube having a closed distal end; illuminating means for illuminating the field to be viewed; optical means contained within the rigid optics tube for transmitting and focusing light reflected from the illuminated field back to the image detector in a manner such that the image to be portrayed on a screen coupled to the detector is not reversed; a rigid, removable, sterilzable or discardable sheath over both said rigid optics tube and illuminating means and completely isolating said tube and illuminating means from contact with the field or walls of the cavity; and means for allowing light to pass from said illuminating means out of said sheath and means for allowing light reflected from the field to pass through said sheath and rigid tube and into said optical means. Still another embodiment of the invention comprises means for creating a three dimensional image.

DETAILED DESCRIPTION OF THE INVENTION

Figure 1:
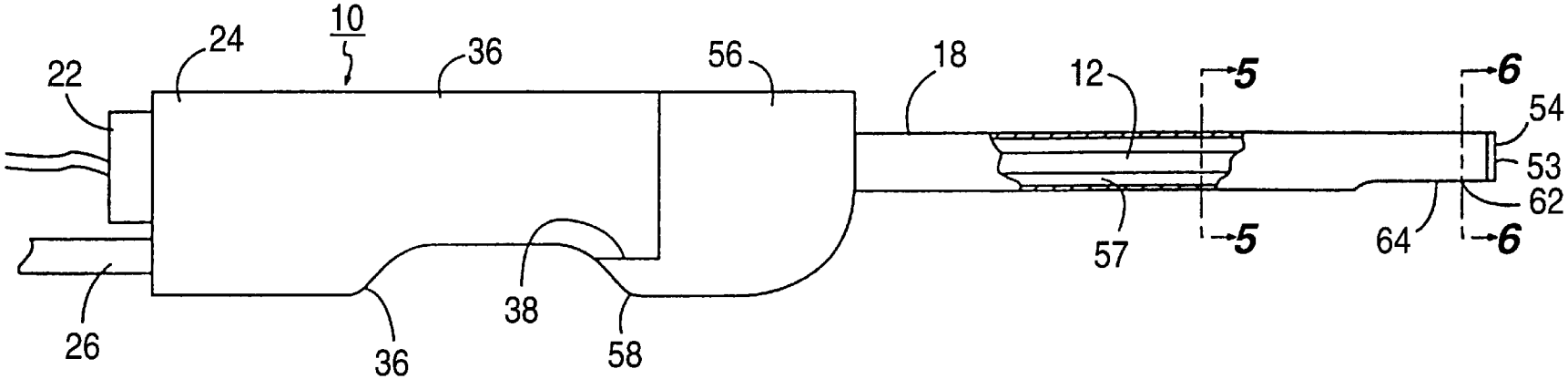
FIG. 1 is a side, partially cut-away, elevational view of a preferred embodiment of the assembled device.
Figure 2:
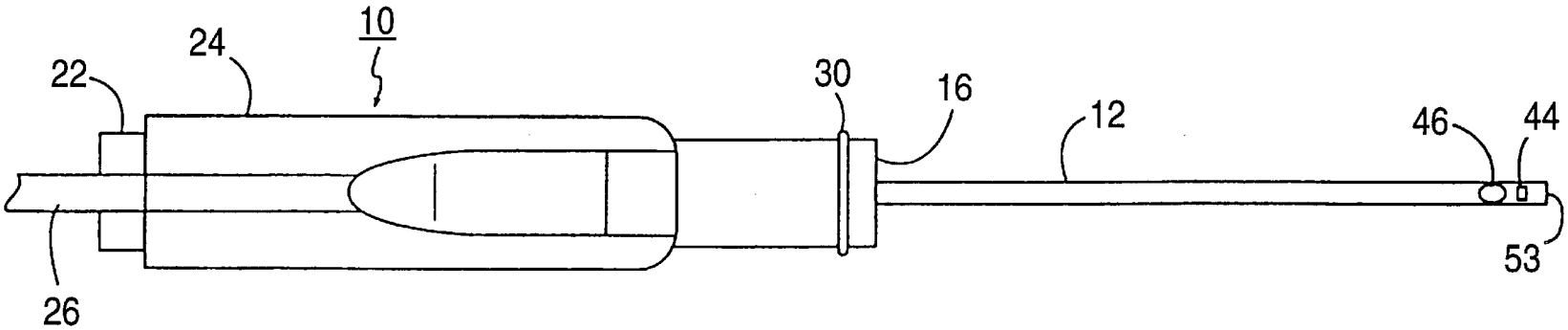
FIG. 2 is a bottom elevational view of the device of FIG. 1 without the sheath.

In general, the preferred novel endoscopic device comprises a handle; means associated with the handle for mounting a video camera thereto or therein; a rigid optic tube mounted to the handle and containing therein optical means for transmitting a focussing light reflected from a surface to be viewed onto the video camera for display on a video screen and/or video recording wherein the displayed image is non-reversed; illuminating means for illuminating the surface to be viewed; video camera means, preferably detachably mounted to the handle; and a rigid, removable, sterilizable or discardable sheath over the rigid tube and illuminating means such that the tube, the optical system therein and the illuminating means are completely isolated from direct exposure to the surfaces to be viewed or surrounding surfaces.

The handle is preferably of a size and shape so as to allow the user to easily and comfortably hold and manipulate the device without touching the portion of the sheath which is inserted into the cavity to be viewed. Typically, the handle is formed from a plastic but may be made of other materials as well, e.g. wood, ceramic or metal.

The means for mounting a solid state video camera to the handle can be any means known in the art. For example, the handle can be provided with a hollow bore having internal screw threads into which a camera can be screwed, or a simple tapered bore can be provided which mates with a tapered camera housing or a key and groove interconnection or a quick release snap-on interconnection can be provided.

The rigid optics tube is generally affixed to the handle opposite the camera. It may be permanently affixed to the handle or removably affixed thereto. If permanently affixed, the dimensions of the endoscopic portion of the device as well as the optical system contained within the tube are likewise fixed. Where the optics tube is removably affixed so that an alternate tube can be placed on the handle, the length of the tube as well as the focal plane and magnification, if any, of the optical system can be changed.

The optics tube is preferably completely enclosed so that the optical system is protected thereby. Also, it is generally preferable, but not necessary, that the optics tube also contain therein the illumination means. The illumination means generally comprises a bundle of light transmitting fibers which transmits light from a light source, through the fiber bundle and out of the device so as to illuminate the area to be viewed. Typically, the optics tube is made of a rigid durable material such as stainless steel, but can be made of virtually any rigid material. When the tube is opaque, at least one transmitting window must be provided therein to allow light reflected from the surface to be viewed to be collected by the optical system for transmission onto the camera and when the optics tube also contains the illuminating means therein, a light transmitting window for the illuminating light must also be provided. This can be two separate windows or a single enlarged window. Any light transmitting material, e.g. glass or quartz, is suitable as a window material. Where the optical tube is itself transparent, a separate window is not required but the tube should be flat and polished in the area through which the light is transmitted so as not to distort the image. A feature of the novel invention is the use of a rigid, removable sheath which as indicated completely surrounds and isolates the optical tube, optical system and illuminating means. The sheath should itself be devoid of any optical components other than possibly one or more light transmitting windows aligned with the illuminating mean/and optical system to allow light to pass out of and into the device, respectively. The sheath should either be made of a material which is sterilizable, i.e. autoclavable, e.g. stainless steel or other non-corrodible metal or alloy, a high temperature plastic or a ceramic, or may be made from an inexpensive rigid plastic which may be discarded after use. Preferably, the sheath fits coaxially over the optics tube, has a closed distal end and is secured to the handle in a manner to substantially prevent its rotation or movement during use.

This invention also contemplates an embodiment wherein a solid state video detector, e.g. a CCD chip is positioned so as to be directly illuminated with light reflected from the field to be viewed without the need for intermediate lens, prisms or the like.

Also contemplated are embodiments employing a straight optical path (or one at an acute angle for use use in the ear, nose and throat (ENT) as well as an embodiment wherein the lens system creates two displaced images for the creation of a 3-D image.

All of the embodiments have in common the use of a handle for continously holding and manipulating the device; a removable, sterilizable sheath protecting the optics; the creation of non-inverted images for viewing on a screen; and preferably, the absence of any occular piece for direct viewing.

A preferred embodiment of the novel device particularly useful as an intraoral endoscopic device is described with reference to FIGS. 1–7.

Referring to FIGS. 1–6 there is shown a novel device 1 comprising a hollow central support member 10 which acts as the handle for holding the assembled device 1 when in use; a narrow elongated lens tube 12 having an appropriate lens system 14 contained therein said tube 12 being mounted within and extending from the distal end 16 of the support member 10. A removable sheath 18, adapted to fit over and completely protect and isolate the lens tube 12 from exposure to the oral cavity or other cavity to be viewed so as not to become contaminated therefrom, is positioned over the lens tube 12. Means are provided with respect to the support member 10 and the sheath 18 such that the sheath 18 will not be disengaged or move while the device 1 is in use. A solid state video camera 22 is removably mounted within the proximal end 24 of the support member 10. In addition, a fiber optic bundle 26 is provided. The fiber optic bundle 26 is coupled to a light source (not shown) at one end thereof and extends into and terminates within the narrow lens tube 12.

The support member or handle 10 is made in a shape and size which facilitates holding the device in operation without having to touch any portion of the device which may be inserted in the cavity to be viewed. e.g. the mouth. It may be made of any convenient rigid material including plastics and metals.

The distal end portion 16 of the handle 10 is cylindrical and is provided with a shallow groove 28 circumferentially the area around into which is placed an O-ring 30. A narrow lens tube hole 32 is centrally bored axially through the distal end portion 16 of the handle 10. This narrow lens tube hole 32 communicates with a centrally bored wide camera hole 34 which extends through a main body portion 36 of the handle 10. The distal part of the main body portion 36 of the handle 10 is provided with a flat surface 38. In addition, a fiber optic entrance hole 40 which communicates with the camera hole 34 is provided through the proximate end of the handle 10 below the camera hole 34.

The proximate end of the camera hole 34 is provided with means, such as a threaded portion 42, so as to removably accept the solid state video camera 22 therein.

The lens tube 12 is of a diameter such that it securely fits within the lens tube hole 32 of the handle 10. As can be seen from FIG. 3, the optical system 14 contained within the lens tube 12 comprises the fiber optic bundle 26 through which light from a light source (not shown) is transmitted through the lens tube 12 and emanates from the lens tube 12 via a lens tube transmissive window 44. Light reflected from the surface to be viewed is transmitted back into the lens tube 12 via an optical window 46 adjacent and proximate to the transmissive window 44. The reflected light entering optical window 46 adjacent and proximate to the transmissive window 44. The reflected light entering optical window 46 then passes through a series of optical imaging devices including a right angle roof prism 48, a set of objective lenses 50, a rod lens 15 and a video relay lens 52. Inherent in the function of the roof prism 48 is the reinversion of the reversed image to be viewed such that the image to be viewed on the screen is not inverted with respect to the actual visual appearance of the field being viewed by the user of the device. In this way, movement of the image of the device on the screen with respect to the field, e.g. to the left, mimics the direction of actual movement of the device in the cavity being viewed. Absent the roof prism, the lens system as shown, inverts the image resulting in a mirror image of the field on the viewig screen. It should be understood that while use of the lens system with the roof prism as set forth above is preferred, any lens sysyem which provides a nonreversed non-inverted) image on the viewing screen is contemplated as part of this invention. For example, other suitable lens system include the use of a pair of lenses, the first reversing the image while the second returning the image to a nonreversed state. The final image is made to focus upon the solid state camera 22 which is mounted on the opposite end of the handle 10. The end 53 of the lens tube 12 is closed so as to prevent contamination of the optics. As can be seen with reference to FIGS. 5 and 6, the optical fibers 26 extend axially through lens tube 12 adjacent rod lens 15 until they approach the area of window 44 where the fibers are bent 90 degrees downwardly so as to terminate with their ends adjacent the window 44 in a direction essentially perpendicular to the axis of the lens tube 12. It will be understood that the invention is not limited to any specific lens system and any lens system which conveys the light to the video detector of the camera so as to give a non-reversed sharp image is suitable. In fact, a lensless system wherein the video detector is directly illuminated also falls within the scope of the invention. Further, for non-oral cavity applications, it may be preferred to use a straight path or acute angle path lens and illuminating system wherein the illuminating light eminates in a direction essentially parallel to or at an acute angle to the axis of the lens tube 12 and the light reflected from the field is picked up by the lens system at essentially the same angle.

The sheath 18 is closed at its distal end 54 and when in operating position, concentrically surrounds lens tube 12. The proximal end 56 of the sheath 18 snugly fits over the distal end portion 16 of the handle 10. The O-ring 30 forms a seal so as to prevent contamination from entering the cavity formed by the space 57 (see FIG. 1) between the outside of the lens tube 12 and the inside of the sheath 18, thus preventing contamination of the lens tube 12 and obviating the need for sterilization of the lens tube 12. The proximal end portion 56 of the sheath 18 is provided with an extension 58 having a flat upper surface 60 which snugly mates with the flat surface 38 provided on the handle 10. This prevents rotation of the sheath 18 during use. The sheath is also provided with light transmitting glass or quartz windows 62 and 64 which are in registration with windows 44 and 46 of the lens tube so that light emanating from the lens tube 12 can pass out of the sheath 18, and the light reflected from the surface to be studied can pass through the sheath 18 into the optical lenses of the lens tube 12.

Figure 7:
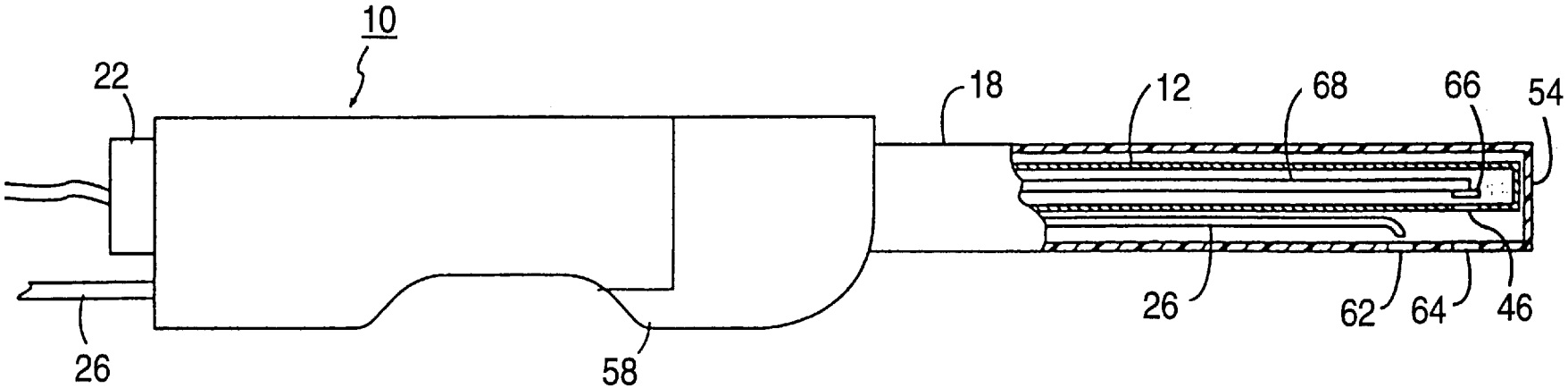
FIG. 7 is a side, partially cross-sectional view, of another embodiment of the device.

The embodiment shown in FIG. 7 is essentially the same as the previously described embodiment except that the lens system is replaced by a solid state video detector 66 positioned adjacent window 46 in tube 12 and means 68 are provided for transmitting the signal produced in the detector to the signal process or of the video camera. Also, the fiber optic illuminating means 26 is outside of, but adjacent the tube 12.

Figure 3:
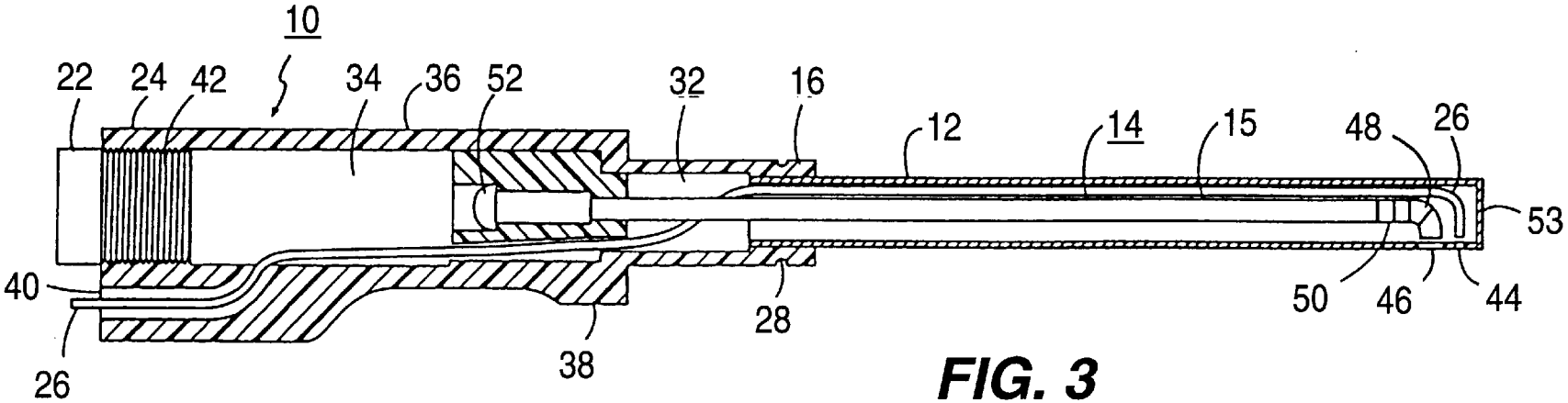
FIG. 3 is a side cross-sectional view of the device of FIG. 1 without the sheath.
Figure 4:
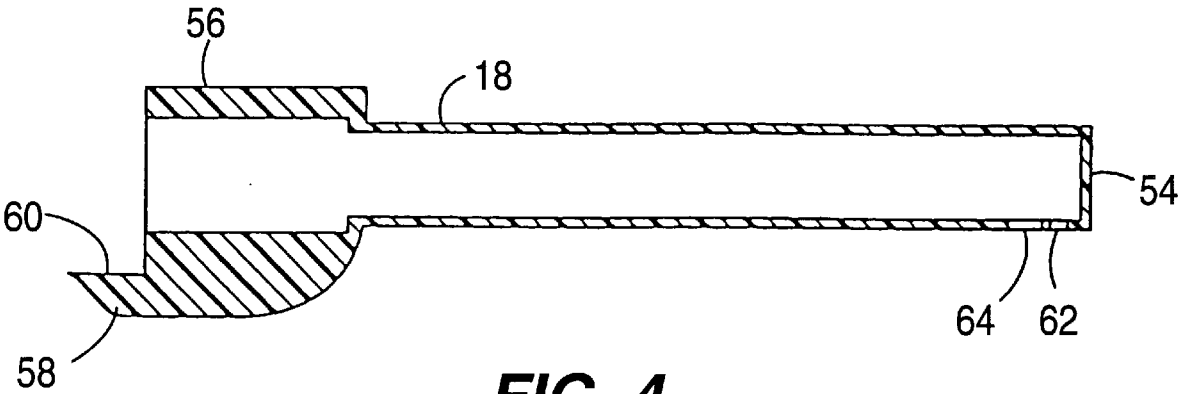
FIG. 4 is a side cross-sectional view of the sheath.
Figure 6:
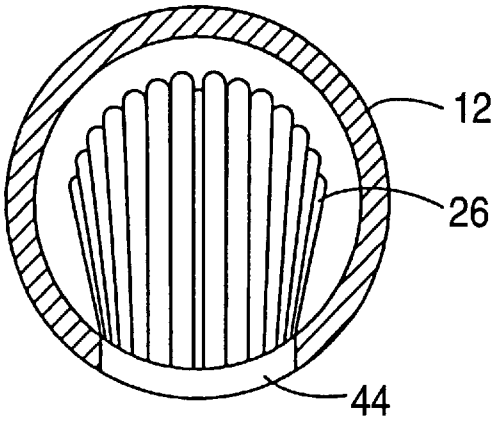
FIG. 6 is a front cross-sectional view of the optics tube of the device of FIG. 1 along section 6—6.
Figure 5:
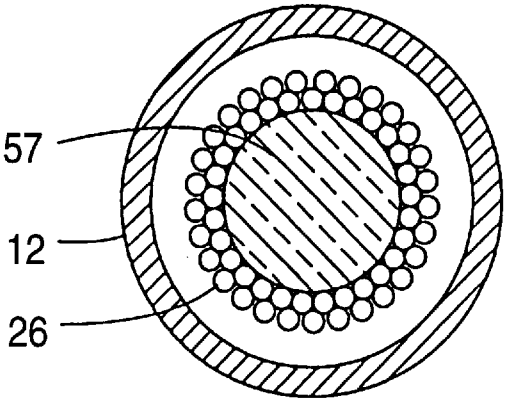
FIG. 5 is a from cross-sectional view of the optics tube of the device of FIG. 1 along section 5—5.
Figure 8:
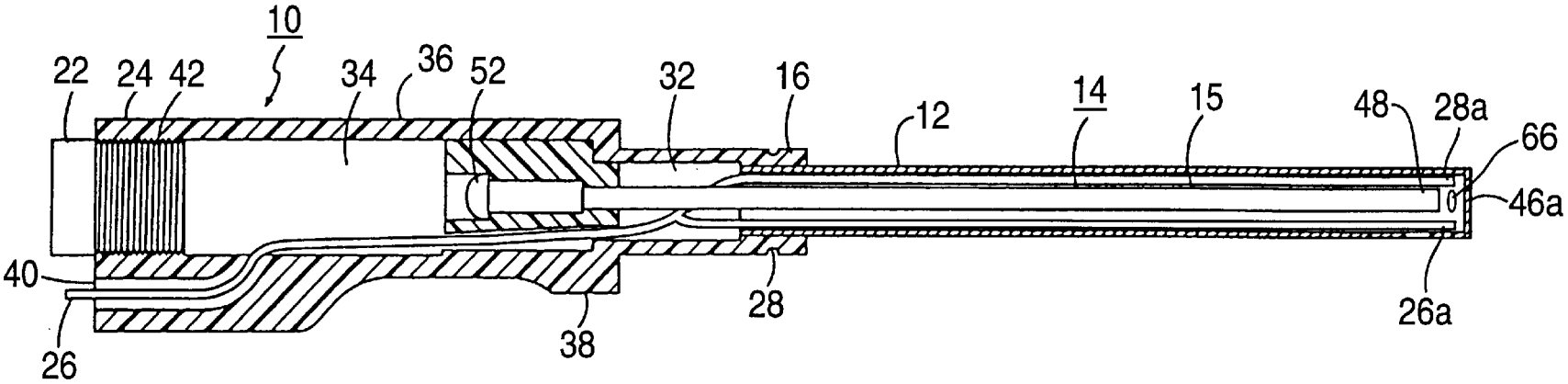
FIG. 8 is a side, partially cross sectional view of yet another embodiment of the invention useful for ENT purposes wherein the optical path is straight.

Referring to FIG. 8, there is shown a device similar to that shown in FIG. 3 except that the distal end is configured so that the light path is along the axis of the lens tube 12. More particularly, the fiber optic bundles 26a which supply illumination are not curved at there ends as in the embodiment of FIG. 3, but instead continue parallel to the axial direction of the lens tube 12 until there termination. Similarly, the lens system eliminates the right angle roof prism and any associated mean for providing a 90 degree angle with respect to the axis of the lens tube 12 and replaces this with a lens 67, the axis of which is in line with the axis of the lens tube 12 and which, preferably terminates in the same plane at the distal end of the lens tube 12 as does the fiber optic bundles 26a. Of course, in this embodiment, a transmission window 46a is located at the distal end face of the lens tube 12 and a corresponding transmission window 64a is located at the distal end face 54 of the sheath 18. While only one large window is shown for each of the lens tube and the sheath, one could employ separate windows for the fiber optic bundle and the lens system, if desired. This straight light path configuration is particularly suitable for ENT endoscopes.

Figure 9:
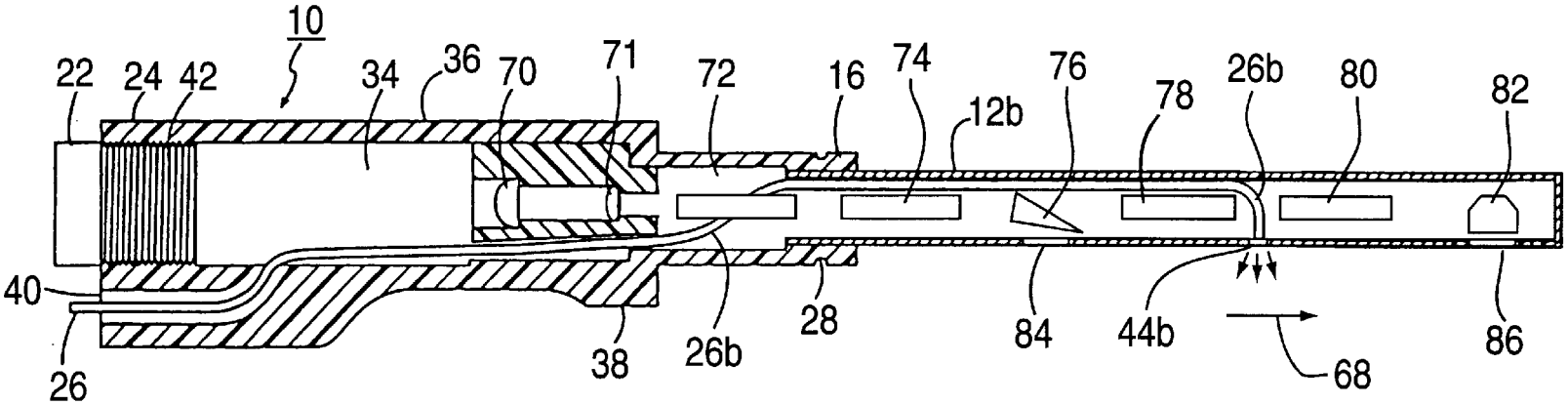
FIG. 9 is a side cut-away view of an embodiment of the invention suitable for creating a three dimensional image.

Referring to FIG. 9, there is shown an optics tube having a lens system which allows for the provision of a three dimensional image when the output of the video camera associated therewith is coupled to a video processor as is known in the art for producing three dimensional video images from a pair of displaced two dimensional images of an object. Here, however, the two images are produced along a single lens path. In accordance with this embodiment, a lens tube 12b contains therein a fiber bundle 26b for transmitting illuminating light to an object 68 to be viewed. A window 44b is provided in the lens tube 12b for allowing the light to be transmitted outside the lens tube 12b. An objective lens 70 for focussing the image on the detector(s) is essentially centrally located in the lens tube 12b proximately of the video detector (not shown)). Distally from the objective lens 70 in order of location is an optical system comprising a collimating lens 71, a first pair of rod lenses 72 and 74, a triangular prism 76, a second pair of rod lenses 78 and 80 and a pentaprism 82. The various members of the lens system all have their optical axes alligned with the axis of the lens tube 12b except for the triangular prism which preferably, is somewhat tilted. Windows 84 and 86 are provided in the lens tube 12b so as to be registered with and allow light reflected from the object to enter the triangular prism 76 and the pentaprism 82, respectively. The objective lens may either be a thin lens for focussing the displaced images created by the system on a single plane on the face of a solid state video detector, or may be a thick lens creating a pair of longitudinally displaced images which can be focussed on a pair of longitudinally displaced video detectors.

In operation, light eminating from window 44b of lens tube 12b, strikes the object 68 and is reflected therefrom. The reflected light enters the lens system through windows 84 and 86 and into prisms 76 and 82 respectively. The light is then transmitted along the optical path to the objective lens and focussed on the video detector. Light entering through the pentaprism 82 creates a non reversed image, while light entering the triangular prism 76 through window 84 creates a reversed image which may be processed to a nonreversed image by means of known electronic video processing techniques. By tilting the triangular prism jus a few degrees, one can obtain a better separation of the reversed and nonreversed images. The video processor converts the images to a three dimensional video display.

The novel device and system have several advantages over prior art devices. One primary advantage is an easily removable sheath which can be made of a rigid plastic material or of a metal such as stainless steel and which can be discarded (when made of and inexpensive plastic) or autoclaved or otherwise sterilized, separate and apart from the optical system, and which completely protects and isolates the tube containing the optical system from exposure to contamination.

A second advantage is the provision of a universal handle which negates the necessity of touching any part of the device which is inserted into the cavity to be viewed and also provides for quick and easy changing of video cameras according to the application. In addition, the lens tube could also be made interchangeable so that one can readily alter the lens system to fit ones need depending upon the application. Such interchangeability of camera and/or lenses greatly broadens the practical use of the device without substantial cost.

Another important advantage is the provision of a non-inverted screen image whereby the movement depicted on the screen mimics the actual direction of movement of the device in the field being viewed.

Still another advantage is that due to the preferred lens system, the width of the endoscopic portion of the device can be made relatively narrow e.g. ¼", so that it does not block the users field of view.

It should be understood that the embodiment shown and described herein is but one embodiment of the invention and it is not meant to be limiting but only exemplary. For example, while it is preferred that the handle be of a size large enough and shaped so that the user can easily hold and manipulate the device, the size and shape are not critical. Also, while engagement of the video camera to the handle is shown to be by means of a screw thread, virtually any means known for making readily disengageable connections, e.g. quick-disconnects, key and slot, snap-on, set screw, or other connections known in the art are suitable. Similarly the means for removably mounting the sheath over the lens tube and to the handle is not critical and may be altered in any manner which would accomplish sealing of the lens tube from the environment without rotation of the sheath. Also, where the sheath is a light transmitting plastic, the separate windows provided in the sheath can be eliminated. Further, while for use as an intraoral device the typical length of the lens tube and sheath is from 4 to 6 inches, these members can be made of virtually any length provided the optics can be made to accommodate the length either by different lens systems or transmission of a focused image to the camera such as by means of optical fibers.

What is claimed is:

1. An endoscopic device for viewing a field within a cavity comprising:

a handle;

a solid state video detector within said handle;

a rigid optics tube extending distally from said handle and closed at its distal end;

illuminating means for illuminating the field to be viewed;

optical means within said optics tube for conveying light from the illuminated field to the video detector in a manner so as to provide a non-reversed image at the detector; and a [rigid,] removable, sterilizable or discardable sheath encasing said rigid tube and said illuminating means so as to completely isolate them from contact with the field or wall of the cavity.

2. The device of claim 1 wherein said illuminating means is within said rigid tube.

3. The device of claim 2 wherein said illuminating means is a fiber optic bundle.

4. The device recited in claim 1 wherein said illuminating means is external to said rigid tube.

5. The device recited in claim 1 wherein the said solid state detector is part of a video camera interchangeably mounted in the handle at the proximal end of said handle.

6. The endoscopic device recited in claim 1 wherein the optical means creates a straight optical path coaxial with the optics tube.

7. An endoscopic device for viewing a field within a cavity comprising:

a handle;

means associated with said handle for mounting a video camera;

a rigid optics tube mounted to said handle, said optics tube being closed at its distal end;

illuminating means for illuminating the field to be viewed;

optical means contained within the rigid optics tube for transmitting and focusing a non-reversing image of light reflected from the illuminated field to the video camera;

a [rigid,] removable, sterilizable or discardable sheath positioned over both said rigid optics tube and illuminating means and completely isolating said tube and illuminating means from contact with the field or wall of the cavity; and means for allowing light to pass from said illuminating means out of said sheath and means for allowing light reflected from the field to pass through said sheath and rigid tube and into said optical means.

8. The endoscopic device recited in claim 7 wherein the handle is of a size and shape which allows the user to comfortably hold and manipulate the device without touching the portion of the sheath which is inserted into the cavity to be viewed.

9. The endoscopic device recited in claim 7 wherein the sheath is removably mounted on the handle in a manner such that the sheath cannot rotate.

10. The endoscopic device recited in claim 9 wherein the optical means includes a roof prism, a rod lens at least one objective lens and a relay lens.

11. The endoscopic device recited in claim 9 wherein the illuminating means comprises a fiber optic bundle contained within said optic tube.

12. The endoscopic device recited in claim 9 wherein the sheath is comprised of a metal or metal alloy.

13. The endoscopic device recited in claim 12 wherein said sheath is stainless steel.

14. An endoscopic device for creating a three dimensional image of an object on a video screen comprising:

a handle;

a solid state video detector within said handle;

a rigid optics tube extending distally from said handle;

illuminating means;

optical means contained within said optics tube for focussing light reflected form the object onto a video detector means such that two images, one displaced from the other, are focussed upon said video detection means, at least one such image being non-reversed; and a [rigid] sterilizable or discardable sheath completely encasing said optics tube which sheath includes means for transmitting light therethrough.

* * * * *